(12) United States Patent
O'Neill et al.

(10) Patent No.: US 12,311,157 B2
(45) Date of Patent: May 27, 2025

(54) MEDICAL DEVICE WITH A THERMAL MASS FLOW SENSOR FOR BUBBLE DETECTION

(71) Applicant: KONINKLIJKE PHILIPS N.V., Eindhoven (NL)

(72) Inventors: Francis Patrick O'Neill, Kissimmee, FL (US); Ronald Paul Consiglio, Clermont, FL (US); Mark Shih-Cheih Lin, Winter Park, FL (US); Carolus Gerardus Thijssen, Maitland, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/215,869

(22) Filed: Jun. 29, 2023

(65) Prior Publication Data

US 2023/0338669 A1 Oct. 26, 2023

Related U.S. Application Data

(62) Division of application No. 16/333,289, filed as application No. PCT/EP2017/074779 on Sep. 29, 2017, now Pat. No. 11,730,895.

(60) Provisional application No. 62/401,450, filed on Sep. 29, 2016.

(51) Int. Cl.
*A61M 5/36* (2006.01)
*A61M 5/168* (2006.01)

(52) U.S. Cl.
CPC ........ *A61M 5/365* (2013.01); *A61M 5/16886* (2013.01); *A61M 2205/3334* (2013.01); *A61M 2205/3368* (2013.01); *A61M 2205/36* (2013.01)

(58) Field of Classification Search
CPC ............ A61M 1/3626; A61M 5/16886; A61M 5/365; A61M 2205/3334; A61M 2205/3368; A61M 2205/36; A61M 2205/3653
See application file for complete search history.

(56) References Cited

U.S. PATENT DOCUMENTS

| | | | |
|---|---|---|---|
| 5,108,372 | A | 4/1992 | Swenson |
| 6,175,688 | B1 | 1/2001 | Cassidy |
| 7,991,510 | B2 | 8/2011 | Duan et al. |
| 2002/0134134 | A1 | 9/2002 | Derek |
| 2010/0143192 | A1 | 6/2010 | Myrick |
| 2012/0116197 | A1 | 5/2012 | Moberg |
| 2012/0283630 | A1 | 11/2012 | Lee |
| 2012/0291540 | A1 | 11/2012 | Cooke |
| 2013/0237955 | A1 | 9/2013 | Neta |

(Continued)

FOREIGN PATENT DOCUMENTS

| | | |
|---|---|---|
| EP | 0405148 | 1/1991 |
| EP | 3076137 | 10/2016 |

(Continued)

*Primary Examiner* — Kami A Bosworth

(57) ABSTRACT

A medical device (10) includes a device housing (12). An in-line thermal mass flow sensor (26) includes a heater (28) and at least one temperature sensor (30). The in-line thermal mass flow sensor is vertically mounted on or in the device housing. The in-line thermal mass flow sensor is configured to measure a flow rate of the fluid through the medical device. At least one electronic processor (18) is programmed to: read the flow rate of the fluid measured by the in-line thermal mass flow sensor; and detect at least one bubble in the fluid based on the measured flow rate.

5 Claims, 4 Drawing Sheets

(56) References Cited

U.S. PATENT DOCUMENTS

2015/0273144 A1 10/2015 Lee
2019/0175828 A1 6/2019 List

FOREIGN PATENT DOCUMENTS

JP 2009276323 11/2011
WO 2010/100611 9/2010

MEDICAL DEVICE WITH A THERMAL MASS FLOW SENSOR FOR BUBBLE DETECTION

CROSS REFERENCE TO RELATED APPLICATION

The present application is a divisional of co-pending U.S. patent application Ser. No. 16/333,289, filed Mar. 14, 2019, which is the U.S. National Phase application under 35 U.S.C. § 371 of International Application No. PCT/EP2017/074779 filed Sep. 29, 2017, which claims the benefit of U.S. Provisional Application No. 62/401,450 filed Sep. 29, 2016. These applications are hereby incorporated by reference herein.

FIELD

The following relates generally to the radiology arts, medical infusion arts, infusion pump arts, and related arts.

BACKGROUND

Infusion pumps typically use pressure based occlusion detection to detect a blockage between the pump and the patient. For example, in a syringe infusion pump, this is done either by monitoring the pressure required to drive the syringe plunger or the pressure in the tube leading to the patient. Similar types of pressure monitoring may be used in volumetric infusion pumps. These methods are slow, and can be inaccurate. Methods are being developed to detect occlusion based on thermal flow rate sensing, but these methods are dependent on characterizing the behavior of a large range of medication and on knowing what medication is being delivered to the patient.

Improvements disclosed herein address the foregoing and other disadvantages of existing infusion pump systems, methods, and the like.

BRIEF SUMMARY

In accordance with one illustrative example, a medical device includes a device housing. An in-line thermal mass flow sensor includes a heater and at least one temperature sensor. The in-line thermal mass flow sensor is vertically mounted on or in the device housing. The in-line thermal mass flow sensor is configured to measure a flow rate of the fluid through the medical device. At least one electronic processor is programmed to: read the flow rate of the fluid measured by the in-line thermal mass flow sensor; and detect at least one bubble in the fluid based on the measured flow rate.

In accordance with another illustrative example, method of detecting bubbles in a medical device includes: with an in-line thermal mass flow sensor, measuring a flow rate of a fluid flowing through a medical device, the in-line thermal mass flow sensor being vertically mounted in a device housing of the medical device; with at least one processor, reading the flow rate of the fluid measured by the in-line thermal mass flow sensor; and with the at least one processor, detecting at least one bubble in the fluid based on the measured flow rate.

In accordance with another illustrative example, a medical pump includes a motor and a housing containing at least the motor. An in-line thermal mass flow sensor includes a heater and at least one temperature sensor. The in-line thermal mass flow sensor is vertically mounted on or in the housing. The in-line thermal mass flow sensor is configured to measure a flow rate of the fluid through the medical pump. At least one electronic processor is programmed to: read the flow rate of the fluid measured by the in-line thermal mass flow sensor; and detect at least one bubble in the fluid based on the measured flow rate. A display is configured to display a warning of a detected bubble in the medical pump.

One advantage resides in detecting bubbles in an infusion pump.

Another advantage resides in reducing false-negative bubble detections.

Another advantage resides in eliminating medicine-type sensitivity based on abrupt changes in flow.

Another advantage resides in detecting retrograde flow in an infusion pump.

Further advantages of the present disclosure will be appreciated to those of ordinary skill in the art upon reading and understand the following detailed description. It will be appreciated that a given embodiment may provide none, one, two, or more of these advantages.

BRIEF DESCRIPTION OF THE DRAWINGS

The present disclosure may take form in various components and arrangements of components, and in various steps and arrangements of steps. The drawings are only for purposes of illustrating the preferred embodiments and are not to be construed as limiting the invention.

DETAILED DESCRIPTION

Using a flow sensor that employs a heater and downstream temperature sensor for bubble detection is recognized herein to be difficult because the flow sensor signal will depend critically upon the type of medication, including the concentration of medicine in the saline solution or other solvent. Moreover, detection of bubbles (which can present a life-critical problem in intravascular infusion) is recognized herein to be critically dependent upon the orientation of the flow sensor. If the flow sensor is oriented horizontally then a bubble will not block flow uniformly, and the uninterrupted flow below the bubble may result in a false-negative bubble measurement.

The following proposes a solution that employs a vertically oriented flow sensor and which measures derivatives of the flow rate and/or ratios of average flow rate at different times. The vertical orientation avoids the situation in which the bubble floats asymmetrically at the top of the flow. Detection based on derivatives or differences in averages avoids the problem of medicine-type sensitivity since bubbles or occlusions will produce an abrupt change in the measured flow rate regardless of the absolute flow sensor signal.

To ensure the desired vertical orientation, the flow sensor is disclosed to be mounted vertically to the side of the infusion pump, e.g. in the tube dock, or built into the pump itself in the desired vertical orientation. With a vertical orientation of the flow sensor, the flow orientation can be either up or down.

Figure 1:
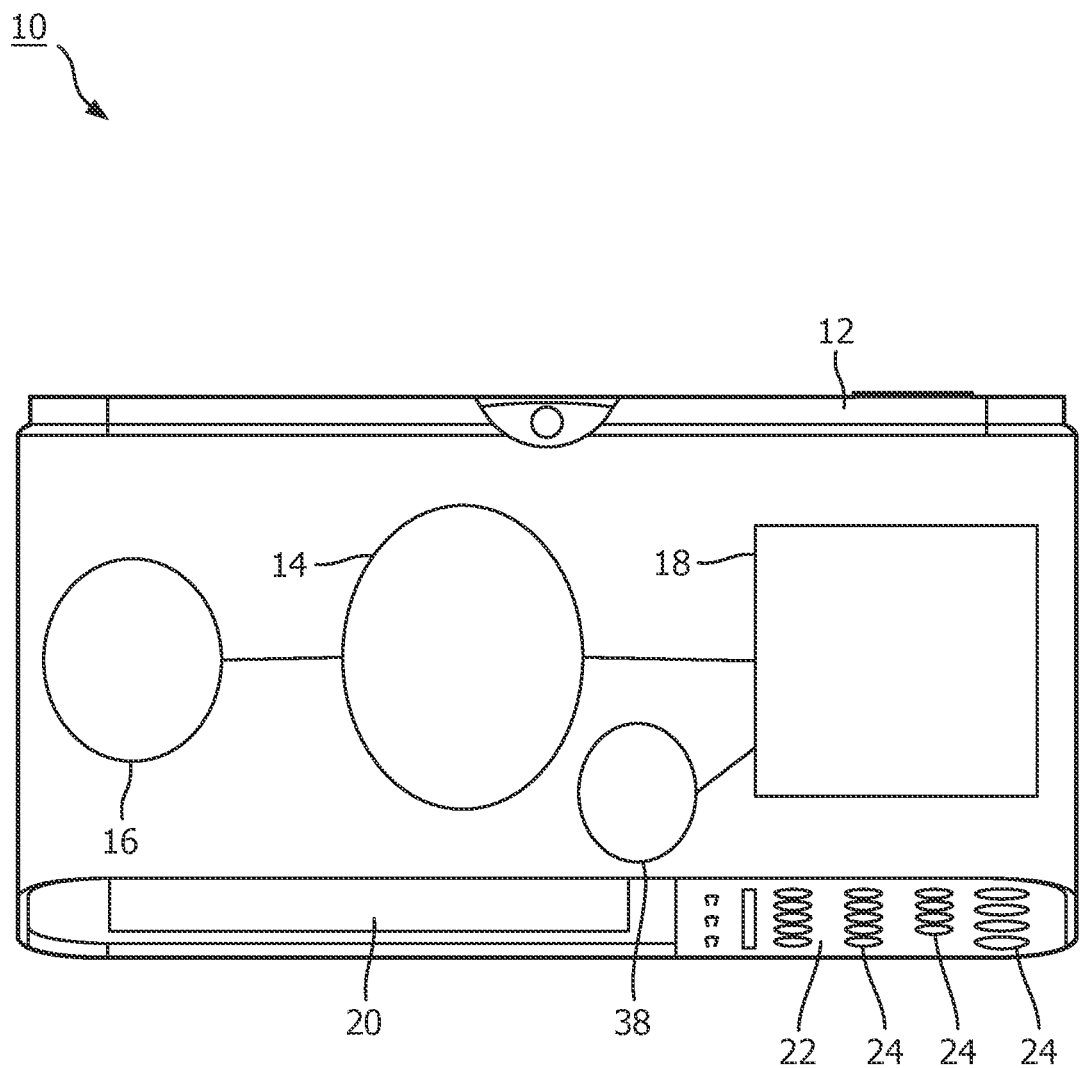
FIG. 1 diagrammatically illustrates a top view of the medical device in accordance with one aspect.

With reference now to FIG. 1, a schematic illustration of a medical device 10 is shown. The illustrative device is a volumetric infusion pump 10, but the disclosed bubble detection approaches may be employed in other types of like devices such as a syringe pump. The medical device 10 includes a device housing 12 that encloses a motor 14, a power source 16, and at least one electronic processor 18. As illustrated in FIG. 1, a "top" portion of the housing 12 is removed, so that the internal components disposed therein are visible. The motor 14 is configured to operate the medical device 10 to deliver intravascular (IV) fluid to a patient at a controlled flow rate. The motor 14 is powered by the power source 16 (e.g., a battery). The at least one processor 18 is programmed to control operations of the infusion pump 10, as described in more detail below.

The illustrative medical device 10 also includes a display 20 configured to display details of operations of the medical device 10, and a keypad 22 disposed adjacent the display 20. The keypad 22 includes a plurality of keys 24. These are optional components, and if included are configured for the particular medical device.

Figure 2A:
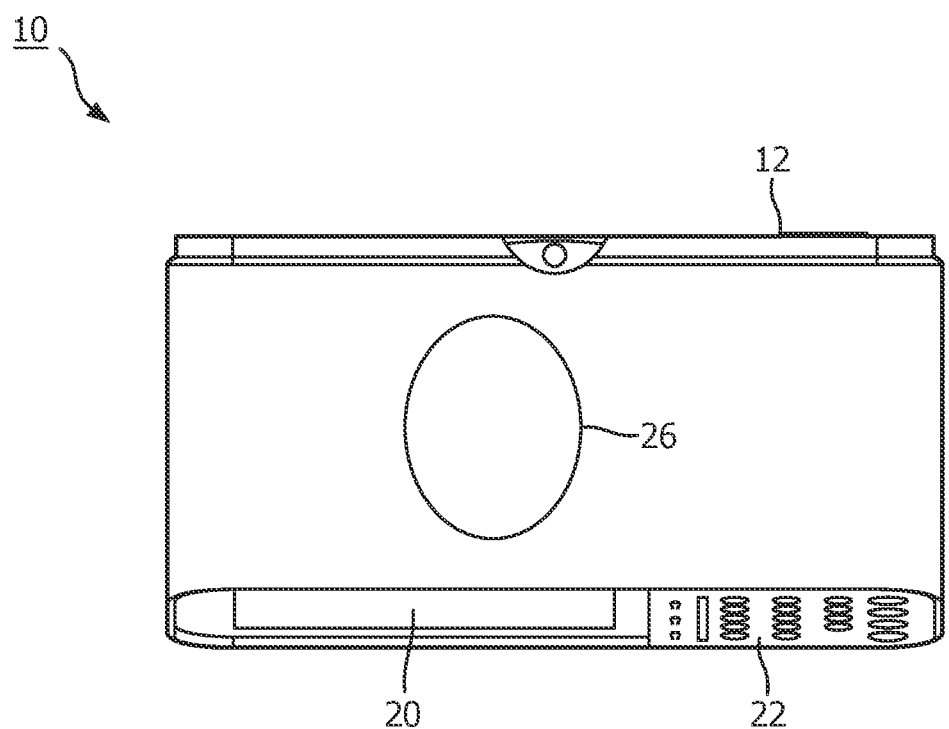
FIGS. 2A and 2B diagrammatically illustrate top and sides views of the medical device of FIG. 1.
Figure 2B:
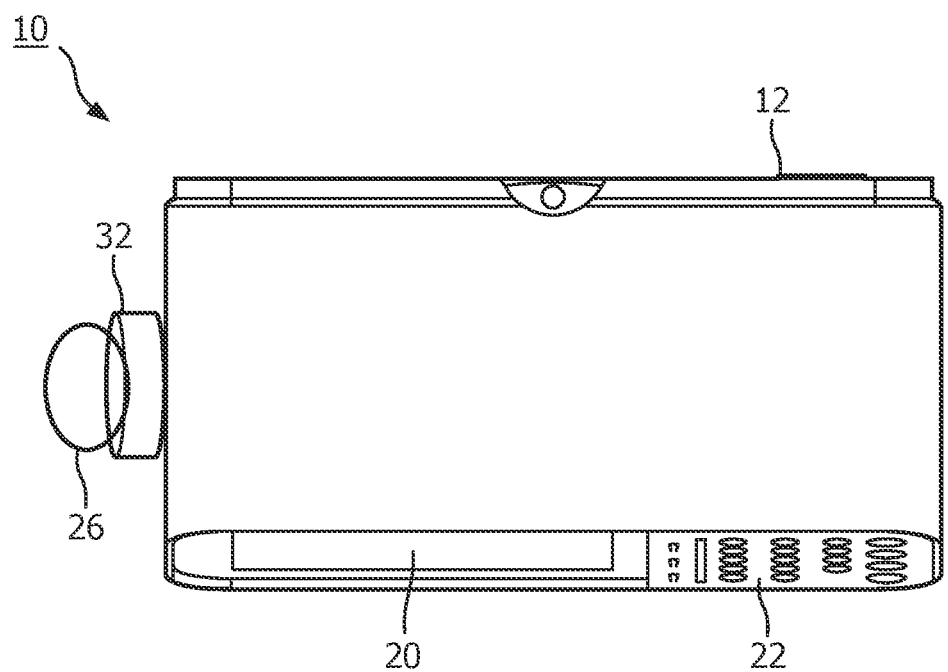

Referring now to FIGS. 2A and 2B, and with continuing reference to FIG. 1, the infusion pump 10 also includes an in-line thermal mass flow sensor 26. The in-line thermal mass flow sensor 26 is vertically mounted on or in the device housing 12. In some examples, as shown in FIG. 2A, the in-line thermal mass flow sensor 26 is vertically mounted to a tube deck 32 in the device housing 12. In other examples, as shown in FIG. 2B, the in-line thermal mass flow sensor 26 is vertically mounted into a portion of the device housing 12. In either embodiment, the in-line thermal mass flow sensor 26 is vertically oriented with flow through the in-line thermal mass flow sensor in either an upward direction or a downward direction. This vertical orientation avoids the situation in which the bubble floats asymmetrically at the top of the flow. The thermal mass flow sensor 26 may be vertically oriented with the fluid flowing downward through the sensor 26. Alternatively, the thermal mass flow sensor 26 may be vertically oriented with the fluid flowing upward through the sensor 26.

Figure 3:
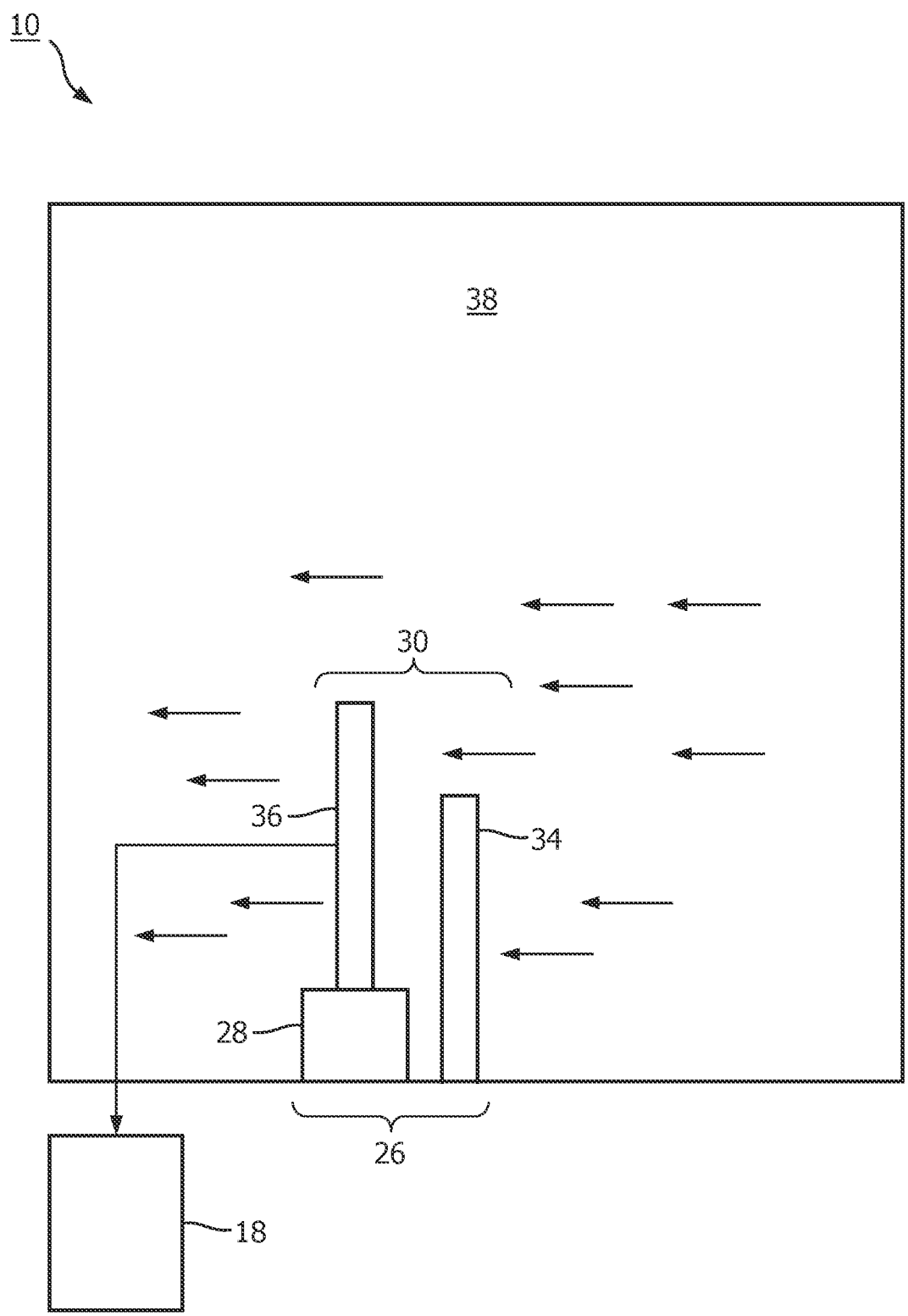
FIG. 3 diagrammatically illustrates components of the medical device of FIG. 1.

Referring now to FIG. 3, and with continuing reference to FIG. 1, the in-line thermal mass flow sensor 26 includes a heater 28 and at least one temperature sensor 30, as known in the art of in-line thermal mass flow sensors. In some examples, the heater 28 and at least one temperature sensor 30 are integrally formed. In other examples, the heater 28 and at least one temperature sensor 30 are positioned adjacent each other. The in-line thermal mass flow sensor 26 can be any suitable, commercially-available sensor (e.g., from Sensirion AG, Staefa ZH, Switzerland).

As shown in FIG. 3, the in-line thermal mass flow sensor 26 is configured to measure a flow rate of the fluid through the medical device 10. To do so, the at least one temperature sensor 30 of the in-line thermal mass flow sensor 26 includes a reference temperature sensor 34 disposed upstream of the heater 28 (flow is upward in FIG. 3), and a sensing temperature sensor 36 disposed with the heater or downstream of the heater. The heater 28 is configured to heat the sensing temperature sensor 36 as fluid flows past the in-line thermal mass flow sensor 26 in a fluid chamber 38 of the infusion pump 10 (shown diagrammatically in FIG. 3 with arrows). The reference temperature sensor 34 is configured to measure a first temperature value of the fluid before the fluid flows passed the heated sensing temperature sensor 36. The heated sensing temperature sensor 36 is configured to measure a second temperature value of the fluid after the fluid flows passed the heated sensing temperature sensor 36 in the fluid chamber 38. From these temperature measurements, the mass flow of the fluid can be determined according to Equation 1.

$$m = h/(c_p * \Delta t) \quad (1)$$

where m is the mass flow rate (in units of kg/s), h is the heat flow rate to the sensing temperature sensor 36, $c_p$ is the specific heat capacity of the fluid, and $\Delta t$ is the temperature difference. For example, if the fluid in the infusion pump 10 is water (which has a specific heat capacity of 4.2 kJ/kg*° C.) can be expressed as:

$$m = h/(4.2) * \Delta t \quad (2)$$

If the heat applied to the sensing temperature sensor 36 is constant, then the in-line thermal mass flow sensor 26 is configured to determine from the difference of the first and second temperature measurements.

The in-line thermal mass flow sensor 26 is configured to transmit the measured mass flow rate value to the at least one electronic processor 18. In some examples, the at least one electronic processor 18 is configured to read the flow rate of the fluid measured by the in-line thermal mass flow sensor 26. From the measured flow rate, the at least one processor 18 is programmed to detect at least one bubble in the fluid. For example, the measured flow rate is compared with a predetermined flow rate threshold value that is programmed into the at least one processor 18. If the flow rate is less than the flow rate threshold value, then there are no bubbles present in the infusion pump 10. Conversely, if the measured flow rate is greater than the flow rate threshold value, then at least one bubble is present in the fluid chamber 28. When a bubble is detected, the at least one processor 18 is programmed to generate a warning of a detected bubble in the medical device 10, which is displayed on the display 20.

In other examples, the at least one processor 18 is programmed to detect at least one bubble in the fluid based on one or more ratios of average flow rates measured at different times. From the measured ratio of average flows, the at least one processor 18 is programmed to detect at least one bubble in the fluid. For example, the measured ratios of average flow rates are compared with a predetermined average flow rate threshold value that is programmed into the at least one processor 18. If the ratios of average flow rate are less than the average flow rate threshold value, then there are no bubbles present in the infusion pump 10. Conversely, if the measured ratios of average flow rate are greater than the average flow rate threshold value, then at least one bubble is present in the fluid chamber 28. When a bubble is detected, the at least one processor 18 is programmed to generate a warning of a detected bubble in the medical device 10, which is displayed on the display 20.

In some examples, the at least one processor 18 knows what commands are input to the pump (e.g., by a doctor or nurse using the keys 24). When the at least one processor 18 detects a sudden change in flow rate without an associated command input by a user, then an alarm can be generated. In one example, the alarm can be a visual alarm displayed on the display 20. In other embodiments, the alarm can be an audio signal or tone broadcast by a speaker 38 of the infusion pump 10 (shown in FIG. 1). When the at least one processor 18 detects a sudden change in flow rate, but an associated command input by a user, then no alarm is generated.

Figure 4:
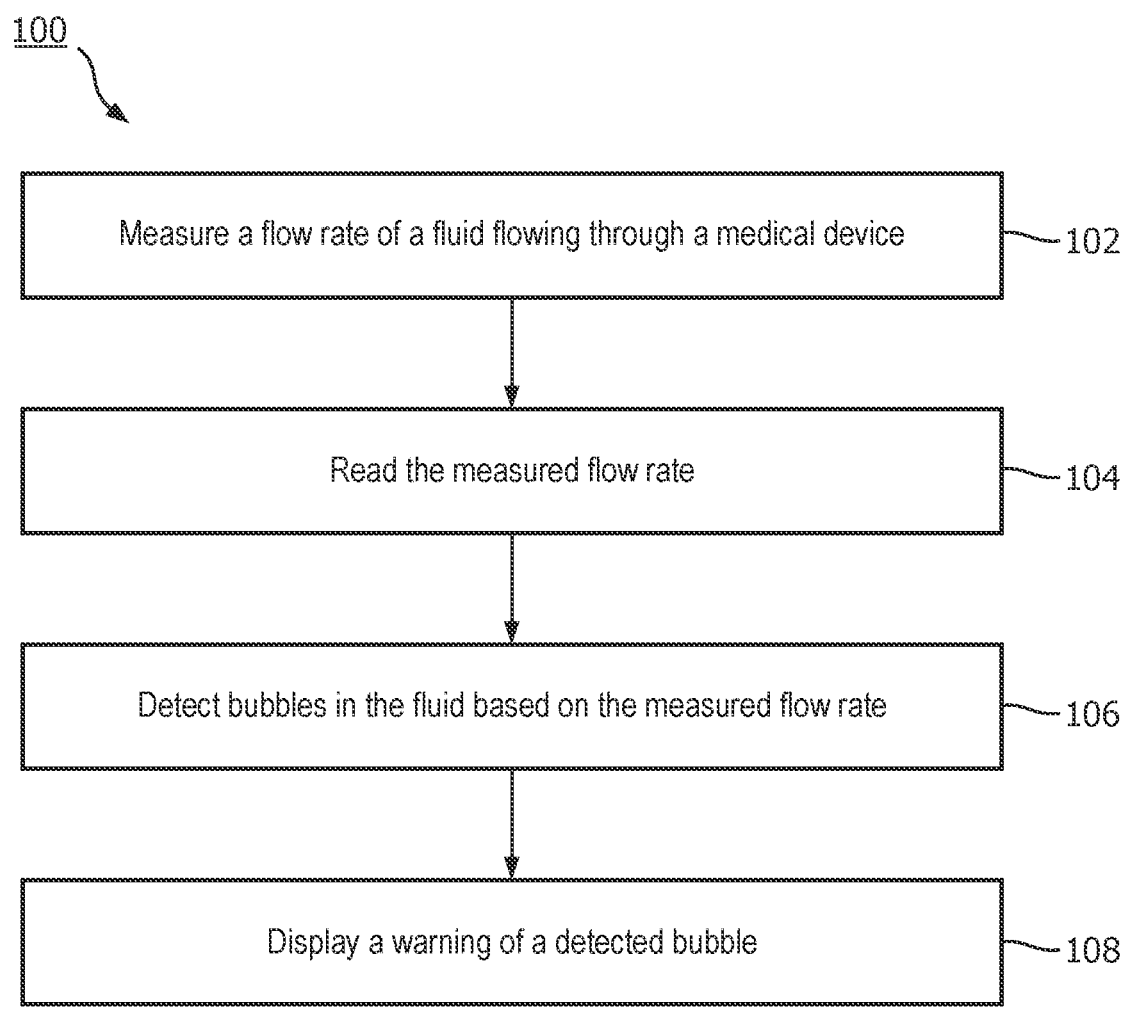
FIG. 4 diagrammatically illustrates a bubble detection method suitably performed using the medical device of FIG. 1.

In addition to being used to detect bubbles as described above, in some embodiments the in-line thermal mass flow sensor 26 is also used for its usual purpose of measuring mass flow rate, as per Equation (1) or (2) above. Such mass flow rate measurements are not accurate if bubbles are present, but in this case the warning of detected bubbles is paramount from a patient care perspective. With reference now to FIG. 4, a method 100 of detecting bubbles in a medical device 10 is shown. At step 102, a flow rate of a fluid flowing through a medical device 10 with an in-line thermal mass flow sensor 26. At step 104, the flow rate of the fluid measured by the in-line thermal mass flow sensor 26 is read with at least one processor 18. At step 106, at least one bubble is detected in the fluid, with the at least one processor 18, based on the measured flow rate. At step 108, a warning of a detected bubble in the medical device 10 on a display 20.

It will be appreciated that the illustrative data processing or data interfacing components of the medical device 10 may be embodied as a non-transitory storage medium storing instructions executable by an electronic processor (e.g. the at least one electronic processor 18) to perform the disclosed operations. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth.

The disclosure has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of detecting bubbles in a medical device, the method comprising:
   with an in-line thermal mass flow sensor, measuring a flow rate of a fluid flowing through the medical device, the in-line thermal mass flow sensor being vertically mounted in a device housing of the medical device with flow through the in-line thermal mass flow sensor being in one of an upward direction or a downward direction;
   with at least one processor, reading the flow rate of the fluid measured by the in-line thermal mass flow sensor; and
   with the at least one processor, detecting at least one bubble in the fluid based on one or more ratios of average flow rates measured at different times.

2. The method according to claim 1, wherein the in-line thermal mass flow sensor includes a heater and at least one temperature sensor, the at least one temperature sensor including:
   a reference temperature sensor disposed upstream of the heater; and
   a sensing temperature sensor disposed with the heater or downstream of the heater.

3. The method according to claim 1, further including:
   vertically mounting the in-line thermal mass flow sensor to a tube deck in the device housing.

4. The method according to claim 1, further including:
   vertically mounting the in-line thermal mass flow sensor into a portion of the device housing.

5. The method according to claim 1, further including:
   with a display, displaying a warning of a detected bubble in the medical device.

* * * * *